United States Patent [19]
Amemiya et al.

[11] Patent Number: 5,840,034
[45] Date of Patent: Nov. 24, 1998

[54] ULTRASONIC IMAGING METHOD AND ULTRASONIC DIAGNOSTIC APPARATUS

[75] Inventors: Shinichi Amemiya; Hiroshi Hashimoto; Koji Miyama; Sei Kato, all of Tokyo, Japan

[73] Assignee: GE Yokogawa Medical Systems, Limited, Tokyo, Japan

[21] Appl. No.: 812,767

[22] Filed: Mar. 6, 1997

[30] Foreign Application Priority Data

May 10, 1996 [JP] Japan ................................. 8-115922

[51] Int. Cl.[6] ................................................ A61B 8/00
[52] U.S. Cl. ........................................... 600/444; 128/916
[58] Field of Search ............................ 128/916; 600/443, 600/444, 447

[56] References Cited

U.S. PATENT DOCUMENTS

| | | | |
|---|---|---|---|
| 5,396,890 | 3/1995 | Weng | 128/916 X |
| 5,474,073 | 12/1995 | Schwartz et al. | 128/916 X |
| 5,485,842 | 1/1996 | Quistgaard | 600/443 |
| 5,529,070 | 6/1996 | Augustine et al. | 600/443 |
| 5,682,895 | 11/1997 | Ishiguro | 128/916 X |

*Primary Examiner*—Francis Jaworski
*Attorney, Agent, or Firm*—Moonray Kojima

[57] ABSTRACT

An ultrasonic diagnostic apparatus either for displaying three-dimensional ultrasonic images allowing an operator to become aware of the distance of a target object from an ultrasonic probe, or for displaying practical three-dimensional ultrasonic images while being simply structured and taking a short time to perform necessary operations. The apparatus comprises: an ultrasonic beam data memory for storing B-mode ultrasonic beam data or CFM ultrasonic beam data; an address control unit for sequentially writing and reading the ultrasonic beam data to and from the ultrasonic beam data memory in the direction of depth; a three-dimensional operation unit for generating three-dimensional ultrasonic beam data using the ultrasonic beam data read from the ultrasonic beam data memory by the address control unit; a three-dimensional ultrasonic beam data memory for storing the three-dimensional ultrasonic beam data thus generated; a DSC (digital scan converter) for converting the three-dimensional beam data to a display-ready format; and a CRT.

12 Claims, 6 Drawing Sheets

ULTRASONIC IMAGING METHOD AND ULTRASONIC DIAGNOSTIC APPARATUS

BACKGROUND OF THE INVENTION

1. Field of the Invention

The present invention relates to an ultrasonic imaging method and an ultrasonic diagnostic apparatus. More particularly, the invention relates to an ultrasonic imaging method and an ultrasonic diagnostic apparatus for displaying a three-dimensional ultrasonic image of a target object allowing an operator to become aware of the distance between an ultrasonic probe and the imaged object, the ultrasonic diagnostic apparatus being simply structured but capable of displaying practical three-dimensional ultrasonic images in a short operation time.

2. Description of the Related Art

To provide a three-dimensional display of an ultrasonic image involves scanning planes (represented by frames) inside a target object by use of an ultrasonic probe. The ultrasonic probe is moved in a direction substantially perpendicular to the planes to accumulate ultrasonic beam data representing a plurality of frames.

FIG. 1 is a conceptual view of volume data Vol. A digital scan converter (DSC) converts ultrasonic beam data of each frame to two-dimensional orthogonal coordinate data about each frame. Given the orthogonal coordinate data, a volume data retaining unit generates volume data Vol in the form of three-dimensional orthogonal coordinate data.

FIG. 2 is a conceptual view of three-dimensional ultrasonic image data P(T). An address control unit and a three-dimensional operation unit perform three-dimensional operations on a set of data representing a position passing through the volume data Vol in a line-of-sight direction at a horizontal visual angle T with reference to the Z direction as illustrated, whereby three-dimensional ultrasonic image data P(T) is generated. The visual angle refers to an angle representing the line-of-sight direction.

Conventional ultrasonic diagnostic systems in operation first prepare volume data Vol, i.e., three-dimensional orthogonal coordinate data. The volume data Vol then undergoes three-dimensional operations so as to be turned into three-dimensional ultrasonic image data P(T) that is ready for display.

One disadvantage of conventional ultrasonic diagnostic systems is that the displayed three-dimensional ultrasonic image fails to reflect the distance between the ultrasonic probe 1 and the target object. Operating such a system, the operator has difficulty in ascertaining how far way the target object is from the ultrasonic probe 1.

Another disadvantage is that because of the need to prepare volume data Vol in the form of three-dimensional orthogonal coordinate data, the conventional system is complicated in structure and takes time in performing the operations involved.

SUMMARY OF THE INVENTION

It is therefore a first object of the present invention to provide an ultrasonic diagnostic apparatus capable of displaying three-dimensional ultrasonic images allowing an operator to become aware of the distance of a target object from an ultrasonic probe.

A second object of the invention is to provide an ultrasonic diagnostic apparatus in a simplified structure but capable of displaying practical three-dimensional ultrasonic images while taking only a limited time to perform necessary operations.

In carrying out the invention and according to a first aspect thereof, there is provided an ultrasonic imaging method comprising the steps of: acquiring three-dimensional data by scanning planes inside a target object with an ultrasonic probe moved in a direction substantially perpendicular to the planes; and generating and displaying, on the basis of the acquired three-dimensional data, a three-dimensional ultrasonic image of organisms and other details of the target object viewed from a desired line of sight, the displayed image being deformed in accordance with the distance of the target object from the ultrasonic probe.

According to a second aspect of the invention, there is provided an ultrasonic diagnostic apparatus comprising: an ultrasonic probe for scanning planes inside a target object; data acquisition means for acquiring three-dimensional data on the target object by moving the ultrasonic probe in a direction substantially perpendicular to the planes; image generation-display means for generating and displaying, on the basis of the acquired three-dimensional data, a three-dimensional ultrasonic image of organisms and other details of the target object viewed from a desired line of sight; and deformation application means for deforming the displayed image in accordance with the distance of the target object from the ultrasonic probe.

Both the ultrasonic imaging method according to the first aspect of the invention and the ultrasonic diagnostic apparatus according to the second aspect thereof are characterized in that the displayed image is deformed in accordance with the distance of the target object from the ultrasonic probe. As the distance is varied, slightly different three-dimensional ultrasonic images are displayed in a way that reflects the varying distance. This allows the operator to become aware of the distance of the target object from the ultrasonic probe.

According to a third aspect of the invention, there is provided an ultrasonic diagnostic apparatus comprising: an ultrasonic probe for scanning planes inside a target object; data acquisition means for acquiring three-dimensional data on the target object by moving the ultrasonic probe in a direction substantially perpendicular to the planes; image generation-display means for generating and displaying, on the basis of the acquired three-dimensional data, a three-dimensional ultrasonic image of organisms and other details of the target object viewed from a desired line of sight; an ultrasonic beam data memory for storing ultrasonic beam data about a plurality of frames; an address control unit for sequentially writing and reading stored ultrasonic beam data to and from the ultrasonic beam data memory in a direction of depth; a three-dimensional operation circuit for generating three-dimensional data by use of the ultrasonic beam data read from the ultrasonic beam data memory by the address control unit; either a three-dimensional ultrasonic beam data memory or a line memory for storing the generated three-dimensional ultrasonic beam data; and a digital scan converter for converting to a screen format the three-dimensional ultrasonic beam data stored in either the three-dimensional ultrasonic beam data memory or the line memory.

Unlike conventional systems, the ultrasonic diagnostic apparatus according to the third aspect of the invention generates three-dimensional ultrasonic beam data by performing three-dimensional operations on ultrasonic beam data. That is, the inventive apparatus does not generate volume data Vol to perform three-dimensional operations thereon. As shown in FIG. 1, volume data Vol is typically made up of about 500×500×50 items of data in XYZ space, whereas ultrasonic beam data is constituted by about 100×500×50 items of data in a space of addresses (ultrasonic beam numbers), echo times (depth) and Z coordinates. The amount of the data thus reduced makes it possible for a simply structured apparatus to display practical three-dimensional ultrasonic images in a short time of operations.

Three-dimensional ultrasonic beam data is generated by performing three-dimensional operations on the ultrasonic beam data. The three-dimensional ultrasonic beam data is converted to a format ready for display. This provides suitable display distortions reflecting the distance of the target object from the ultrasonic probe, allowing the operator to become aware of that distance.

In a first preferred structure of the invention, there is provided an ultrasonic diagnostic apparatus according to the third aspect thereof, wherein a physically identical memory is used as any one of the ultrasonic beam data memory, three-dimensional ultrasonic beam data memory and line memory.

In its first preferred structure, the ultrasonic diagnostic apparatus is structurally simplified because it utilizes the same physically memory as the ultrasonic beam data memory, three-dimensional ultrasonic beam data memory, or line memory.

In a second preferred structure of the invention, there is provided an ultrasonic diagnostic apparatus according to the third aspect or the first preferred structure thereof, wherein the address control unit reads the ultrasonic beam data and the three-dimensional ultrasonic beam data simultaneously from the ultrasonic beam data memory and from either the three-dimensional ultrasonic beam data memory or the line memory, and wherein the three-dimensional operation circuit generates the three-dimensional ultrasonic beam data based on the ultrasonic beam data and three-dimensional ultrasonic beam data read simultaneously.

In its second preferred structure, the ultrasonic diagnostic apparatus successively produces sets of ultrasonic beam data and three-dimensional ultrasonic beam data. This feature enhances processing speed.

In a third preferred structure of the invention, there is provided an ultrasonic diagnostic apparatus according to the second aspect thereof, further comprising: a line memory for temporarily storing the three-dimensional ultrasonic beam data generated by the three-dimensional operation circuit; and an address control unit for transferring the three-dimensional ultrasonic beam data from the line memory to the three-dimensional ultrasonic beam data memory at a next timing.

In its third preferred structure, the ultrasonic diagnostic apparatus uses the line memory to perform so-called cache memory write-back operations. This feature also improves processing speed.

In a fourth preferred structure of the invention, there is provided an ultrasonic diagnostic apparatus according to any one of the third aspect through the third preferred structure thereof, further comprising a bus for data transfer in B mode and CFM (color flow mapping) mode, the bus being used to carry out at least part of the transfer of the ultrasonic beam data and three-dimensional ultrasonic beam data.

In its fourth preferred structure, the ultrasonic diagnostic apparatus is simplified in structure thanks to the use of the bus.

In a fifth preferred structure of the invention, there is provided an ultrasonic diagnostic apparatus according to any one of the second through the fourth preferred structures thereof, wherein the three-dimensional operation circuit is a look-up table (LUT) made of either a RAM (random access memory) or a ROM (read only memory) storing LUT information corresponding to the three-dimensional ultrasonic beam data input either from the three-dimensional ultrasonic beam data memory or from the line memory, as well as LUT information independent of the three-dimensional ultrasonic beam data, and wherein the address control unit selects the type of LUT information to be used.

In its fifth preferred structure, the ultrasonic diagnostic apparatus increases processing speed thanks to the use of the LUT. Because the LUT information independent of the three-dimensional ultrasonic beam data is stored in the LUT, the LUT may be utilized in an initial three-dimensional operation for which there exists no effective three-dimensional ultrasonic beam data. This simplifies control procedures of the apparatus.

In a sixth preferred structure of the invention, there is provided an ultrasonic diagnostic apparatus according to any one of the third aspect through the fifth preferred structure thereof, wherein the address control unit, in generating three-dimensional ultrasonic beam data based on the ultrasonic beam data, calculates an ultrasonic beam address of the three-dimensional ultrasonic beam data to be read either from the three-dimensional ultrasonic beam data memory or from the line memory by use of a formula:

$$N + F \cdot D \cdot \tan\{T\} + \text{Toffset}$$

where, F stands for a frame number of ultrasonic beam data, N for an ultrasonic beam address, D for a frame-to-frame distance, T for a horizontal visual angle, and Toffset for an amount of horizontal offset.

In its sixth preferred structure, the ultrasonic diagnostic apparatus readily calculates the ultrasonic beam address of the three-dimensional ultrasonic beam data paired with the ultrasonic beam data in effect when each horizontal visual angle T is provided.

In a seventh preferred structure of the invention, there is provided an ultrasonic diagnostic apparatus according to any one of the third aspect through the sixth preferred structure thereof, wherein the address control unit, in generating three-dimensional ultrasonic beam data based on the ultrasonic beam data, calculates a depth address of the three-dimensional ultrasonic beam data to be read either from the three-dimensional ultrasonic beam data memory or from the line memory by use of a formula:

$$M + F \cdot D \cdot \tan\{U\} + \text{Uoffset}$$

where, F stands for a frame number of ultrasonic beam data, M for a depth address, D for a frame-to-frame distance, U for a vertical visual angle, and Uoffset for an amount of vertical offset.

In its seventh preferred structure, the ultrasonic diagnostic apparatus readily calculates the depth address of the three-dimensional ultrasonic beam data paired with the ultrasonic beam data in effect when each vertical visual angle U is furnished.

In an eighth preferred structure of the invention, there is provided an ultrasonic diagnostic apparatus according to any one of the second aspect through the seventh preferred structure thereof, wherein the ultrasonic beam data is either one or a combination of a flow rate obtained either in B mode or in color flow mapping mode, a flow rate acquired either from power or from second harmonic, and power.

In its eighth preferred structure, the ultrasonic diagnostic apparatus displays three-dimensional ultrasonic images representing either one or a combination of the flow rate obtained either in B mode or in color flow mapping mode, the flow rate acquired either from power or from second harmonic, and power.

For the ultrasonic diagnostic apparatus according to the third aspect or the first preferred structure of the invention, data transfers need not be sequential in the direction of depth.

On the other hand, for the ultrasonic diagnostic apparatus in any one of its second through the seventh preferred structures, data transfers should preferably be sequential in the direction of depth. In such a case, data are to be transferred in synchronism with clock pulses in the depth direction, so that the address control unit need only transfer an ultrasonic beam address alone or a combination of an ultrasonic beam address and a starting depth address.

Farther objects and advantages of the present invention will be apparent from the following description of the preferred embodiments of the invention as illustrated in the accompanying drawings.

DESCRIPTION OF THE PREFERRED EMBODIMENTS

First Embodiment

Figure 1:
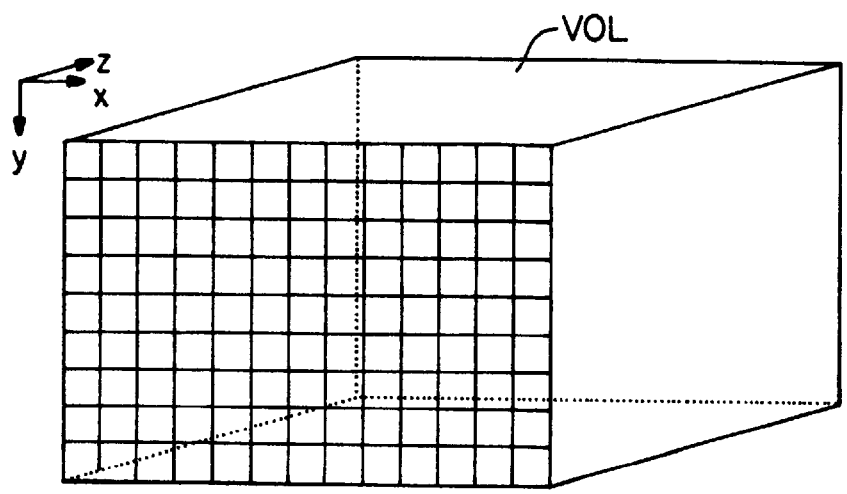
FIG. 1 is a conceptual view of volume data.
Figure 2:
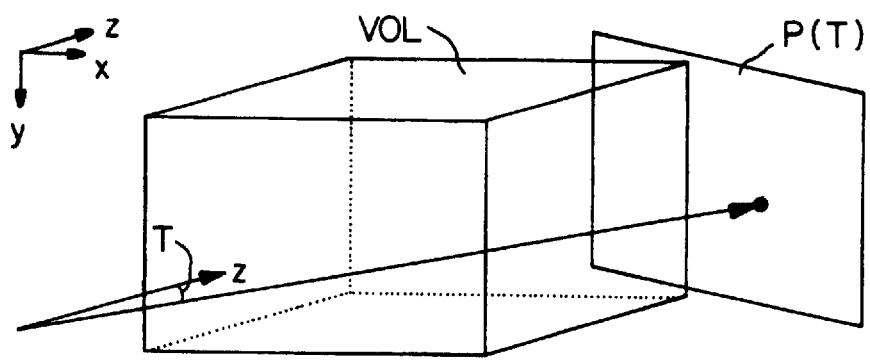
FIG. 2 is a conceptual view of three-dimensional operations on volume data and the resulting three-dimensional ultrasonic image data.
Figure 3:
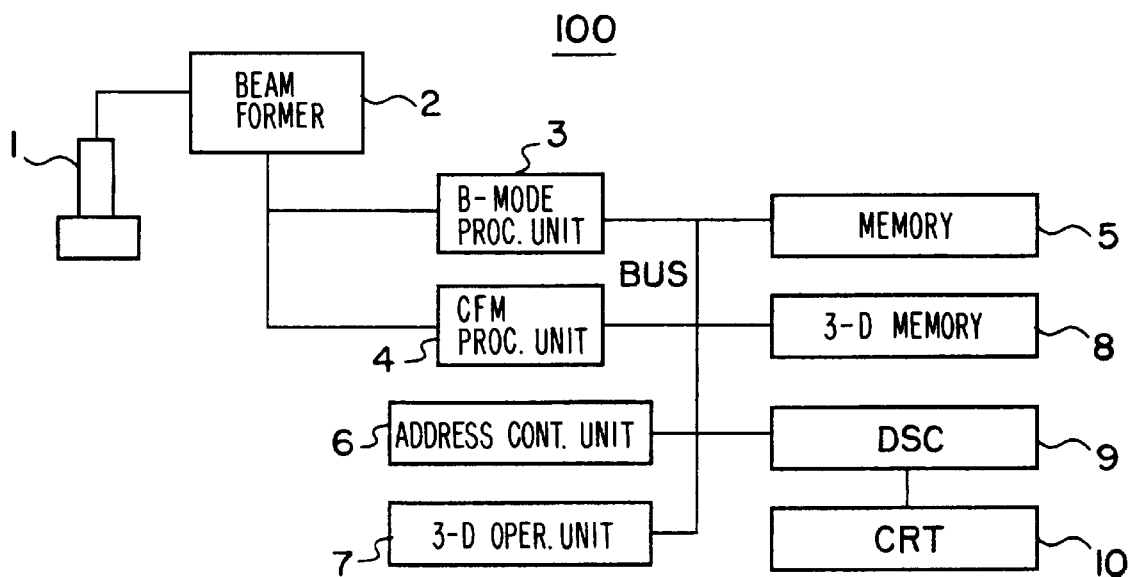
FIG. 3 is a block diagram of an ultrasonic diagnostic apparatus practiced as a first embodiment of the invention.

FIG. 3 outlines an ultrasonic diagnostic apparatus practiced as the first embodiment of the invention. In FIG. 3, an ultrasonic diagnostic apparatus 100 comprises an ultrasonic probe 1 and a beam former 2. The ultrasonic probe 1 transmits ultrasonic pulses to a target object and receives ultrasonic echoes reflected from the target object. The beam former 2 changes the direction of an ultrasonic beam so as to scan planes inside the target object and generates a signal representing an ultrasonic beam in each beam direction. Also in the ultrasonic diagnostic apparatus 100, a B-mode processing unit 3 generates B-mode ultrasonic beam data based on the intensity of the ultrasonic beam signal; a CFM-mode processing unit 4 generates CFM ultrasonic beam data based on Doppler components in the ultrasonic beam signal; an ultrasonic beam data memory (cine memory) 5 stores ultrasonic beam data (i.e., B-mode ultrasonic beam data or CFM ultrasonic beam data); an address control unit 6 sequentially writes and reads the ultrasonic beam data to and from the ultrasonic beam data memory 5 in the direction of depth; a three-dimensional operation unit 7 generates three-dimensional ultrasonic beam data using the ultrasonic beam data read from the ultrasonic beam data memory 5 by the address control unit 5; a three-dimensional ultrasonic beam data memory 8 stores the three-dimensional ultrasonic beam data thus generated; and a DSC (digital scan converter) 9 converts the ultrasonic beam data or three-dimensional beam data to a display-ready format. The ultrasonic diagnostic apparatus 100 also has a CRT 10 for image display.

Figure 4:
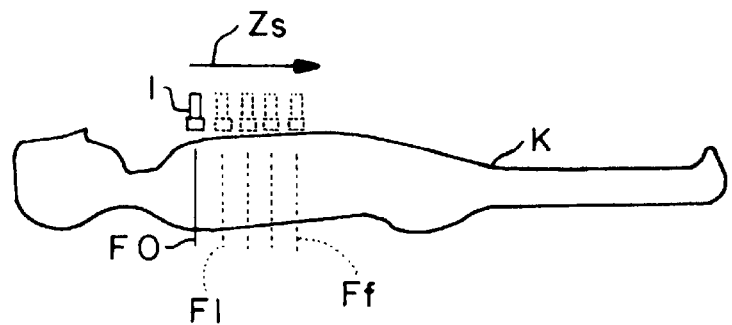
FIG. 4 is a schematic view showing how scanning is done for three-dimensional display.

FIG. 4 schematically shows how scanning is carried out for three-dimensional display. The ultrasonic probe 1 is used to scan planes inside the target object K. During scanning, the ultrasonic probe 1 is moved in a direction Zs substantially perpendicular to the planes. This allows ultrasonic beam data to be accumulated on frames F0 through Ff.

Figure 5:
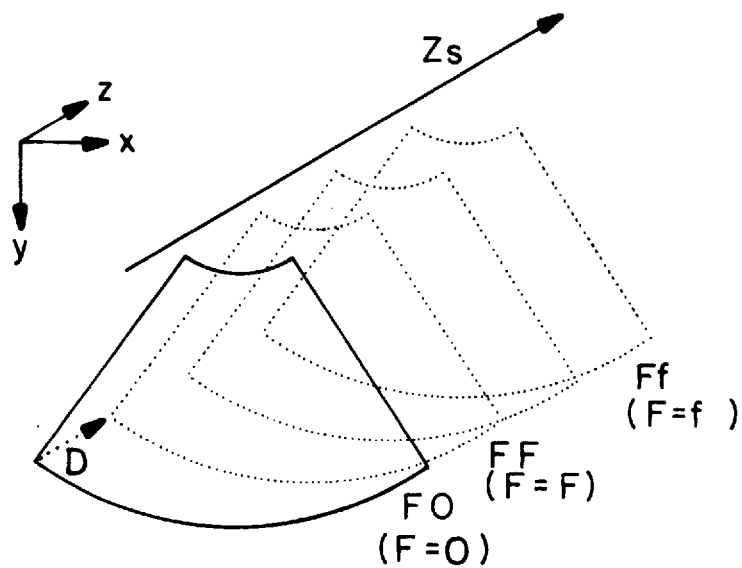
FIG. 5 is a conceptual view of a plurality of frames as they are positioned in space.

FIG. 5 conceptually illustrates the frames F0 through Ff as they are positioned in space. Reference character F stands for a frame number, and D for the distance between two adjacent frames. The scanning planes are an XY plane each, and the direction perpendicular to each plane is along the Z axis.

Figure 6:
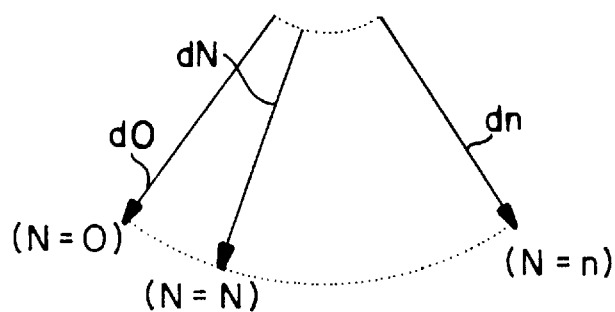
FIG. 6 is a conceptual view of ultrasonic beam data in effect when some beams are positioned in space.

FIG. 6 conceptually shows ultrasonic beam data in effect when some beams are positioned in space. Ultrasonic beam data d0 through dn represent a large number of ultrasonic beams (N=0 through N=n) arranged radially to form a sector-like scanning plane.

Figure 7:
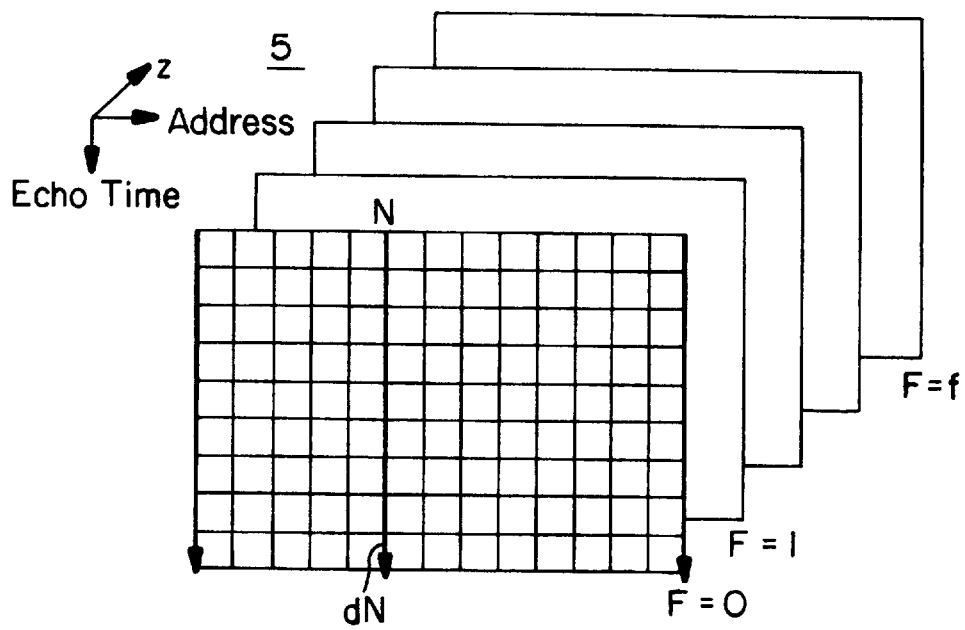
FIG. 7 is a schematic conceptual view of an ultrasonic beam data memory.

FIG. 7 schematically shows a concept of the ultrasonic beam data memory 5. Ultrasonic data dN about each frame is stored at an address denoted by an ultrasonic beam number N. During accumulation of ultrasonic beam data (see FIG. 4) for both normal and three-dimensional display, the ultrasonic beam data output by the B-mode processing unit 3 and CFM-mode processing unit 4 is transferred to the ultrasonic beam data memory 5 for storage therein as well as to the DSC 9. The DSC 9 converts the ultrasonic beam data to a display-ready format. The converted data is displayed on the CRT 10 as ultrasonic images.

When obtaining a three-dimensional display, the operator halts scanning of the ultrasonic probe 1 to freeze the currently displayed image, and orders formation of a three-dimensional ultrasonic image. Given the order, the apparatus starts forming a three-dimensional ultrasonic image in accordance with operator-designated or predetermined parameters. The parameters illustratively include the number of ultrasonic beam data frames (f), a three-dimensional operation method, a starting visual angle, either a visual angle range or a terminating visual angle, and the number of three-dimensional ultrasonic images.

In operation, the address control unit 6 first supplies the ultrasonic beam data memory 5 with the address of ultrasonic beam data d on a first frame (F=0). This causes the ultrasonic beam data memory 5 to output the ultrasonic beam data d on the first frame (F=0). The data d thus output is retained in the three-dimensional operation unit 7.

The address control unit 6 then supplies the ultrasonic beam data memory 5 with the address of ultrasonic beam data d on a second frame (F=1). In turn, the ultrasonic beam data memory 5 outputs the ultrasonic beam data d about the second frame (F=1). The three-dimensional operation unit 7 carries out three-dimensional operations between the retained ultrasonic beam data d on the first frame and the newly input ultrasonic beam data d on the second frame to generate three-dimensional ultrasonic beam data q. The three-dimensional ultrasonic beam data q thus generated is retained by the three-dimensional operation unit 7.

Next, the address control unit 6 supplies the ultrasonic beam data memory 5 with the address of ultrasonic beam data d on a third frame (F=2). This causes the ultrasonic beam data memory 5 to output the ultrasonic beam data d about the third frame (F=2). The three-dimensional operation unit 7 performs three-dimensional operations between the retained three-dimensional ultrasonic beam data q and the newly input ultrasonic beam data d on the third frame to generate (i.e., to update) the three-dimensional ultrasonic beam data. The three-dimensional ultrasonic beam data thus updated is retained by the three-dimensional operation unit 7.

In like manner, the ultrasonic beam data d about one subsequent frame after another is input and processed so as to generate (i.e., update) the three-dimensional ultrasonic beam data q. When the ultrasonic beam data d on all frames have been processed, the resulting three-dimensional ultrasonic beam data q is transferred from the three-dimensional operation unit 5 to the three-dimensional ultrasonic beam data memory 8.

Figure 8:
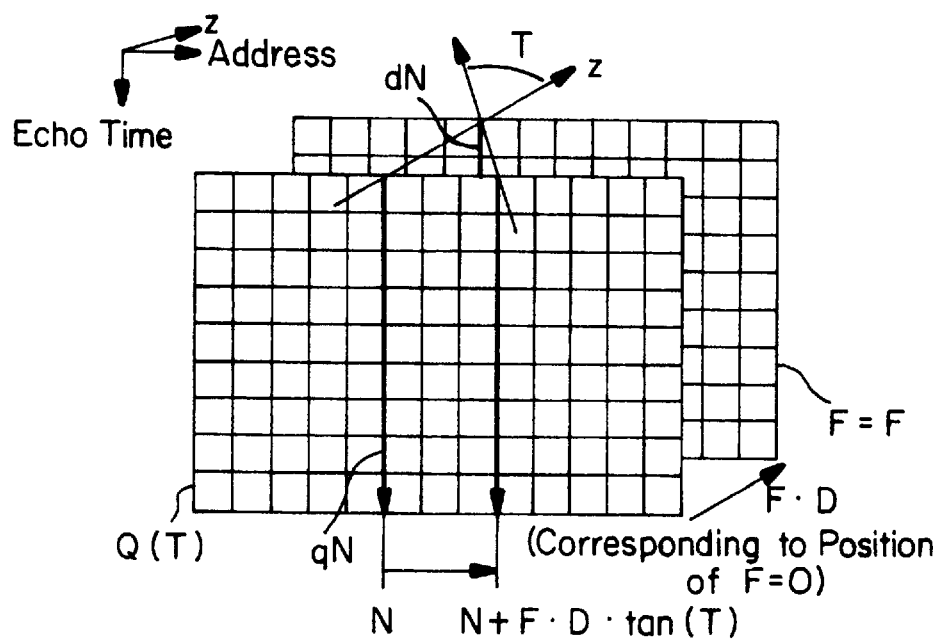
FIG. 8 is a schematic view showing correspondence between ultrasonic beam data and three-dimensional ultrasonic beam data along with addresses, the data being subjected to three-dimensional operations.

In one example, as shown in FIG. 8, three-dimensional operations may be carried out between ultrasonic beam data dN with a beam number N about a frame F, and three-dimensional ultrasonic beam data whose beam address (i.e., beam number) is defined as $$N+F \cdot D \cdot \tan\{T\}+\text{Toffset}$$

where, D stands for the frame-to-frame distance, T for the horizontal visual angle, and Toffset for the amount of horizontal offset (which is 0 in FIG. 8).

In a similar example, three-dimensional operations may be carried out between ultrasonic beam data with a depth address M about the frame F, and three-dimensional ultrasonic beam data whose depth address is defined as $$M+F \cdot D \cdot \tan\{U\}+\text{Uoffset}$$

where, D stands for the frame-to-frame distance, U for the vertical visual angle, and Uoffset for the amount of vertical offset.

Figure 9:
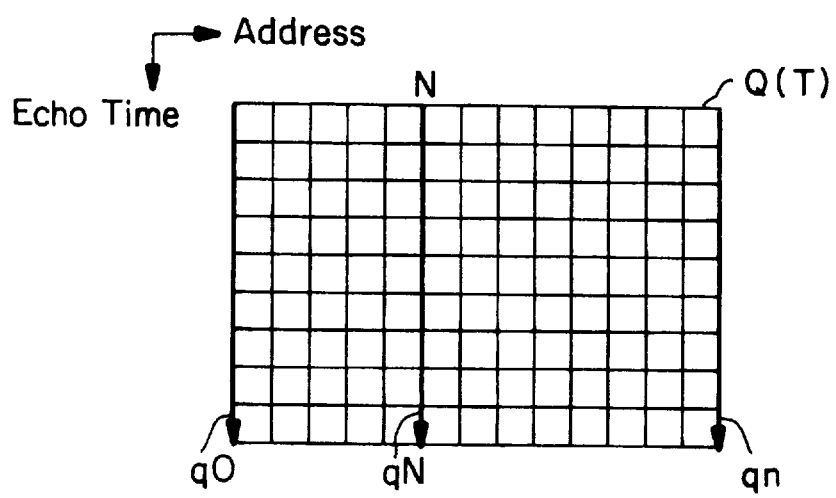
FIG. 9 is a schematic view of three-dimensional ultrasonic beam data representing a single frame.

As illustrated in FIG. 9, after three-dimensional ultrasonic beam data Q(T) on one frame is generated at a given angle T, the generating process is repeated subsequently with different visual angles to build three-dimensional ultrasonic beam data Q on several to scores of frames. The three-dimensional ultrasonic beam data Q thus acquired are stored in the three-dimensional ultrasonic beam data memory 8.

Figure 10:
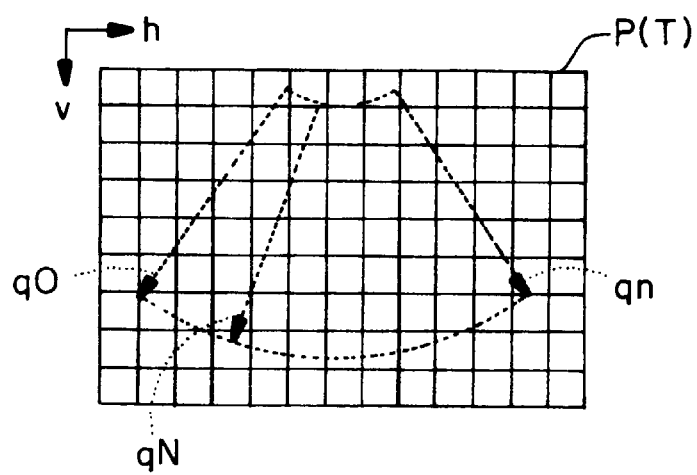
FIG. 10 is a schematic view of three-dimensional ultrasonic image data obtained by converting in format one frame of three-dimensional ultrasonic beam data.

As shown in FIG. 10, the DSC 9 reads three-dimensional ultrasonic beam data Q, on one frame at a time, from the three-dimensional ultrasonic beam data memory 8. The retrieved data is converted to a display-ready format to provide three-dimensional ultrasonic image data P(T). When displayed, the images appear animated.

As described, the ultrasonic diagnostic apparatus 100 practiced as the first embodiment of the invention performs three-dimensional operations on ultrasonic beam data d to generate three-dimensional ultrasonic beam data q. Unlike conventional systems, the embodiment does not create volume data Vol to carry out three-dimensional operations thereon. Because the amount of data to be processed is reduced, the ultrasonic diagnostic apparatus in a simplified structure can display practical three-dimensional ultrasonic images in a short operation time.

Three-dimensional ultrasonic image data P(T) is created by converting three-dimensional ultrasonic beam data Q to a display-ready format. As shown in FIG. 10, the display is deformed so as to reflect the distance of the target object in the direction of depth, i.e., the distance from the ultrasonic probe 1 (deformations are provided so that the greater the distance, the larger the visual angle). This allows the operator to become aware of the distance of the target from the ultrasonic probe 1 while watching the display.

Second Embodiment

Figure 11:
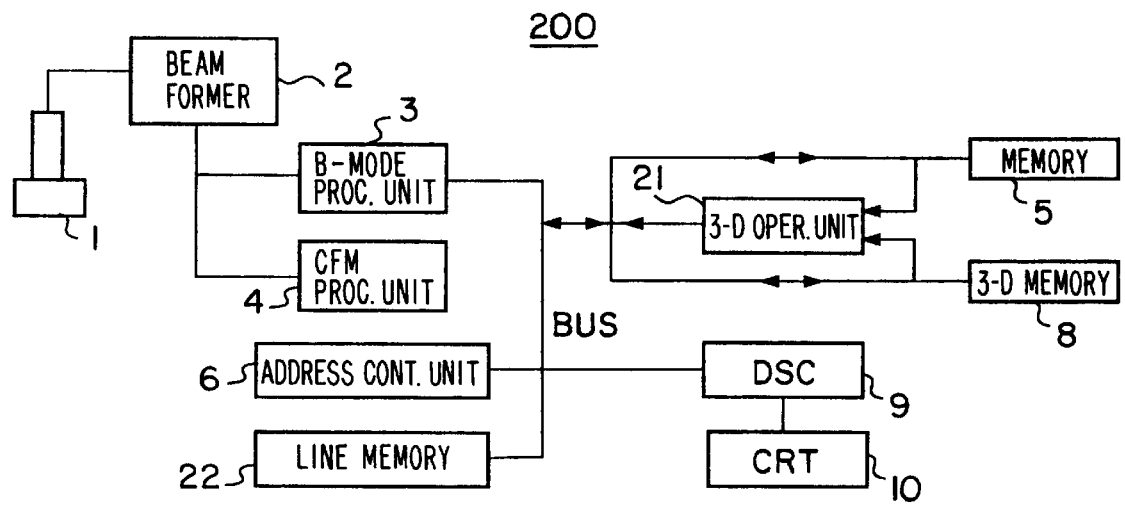
FIG. 11 is a block diagram of an ultrasonic diagnostic apparatus practiced as a second embodiment of the invention.

FIG. 11 is a block diagram of an ultrasonic diagnostic apparatus 200 practiced as the second embodiment of the invention. In operation, the ultrasonic diagnostic apparatus 200 reads ultrasonic beam data from the ultrasonic beam data memory 5 for input to a three-dimensional operation unit 21 while simultaneously reading three-dimensional ultrasonic beam data, subject to three-dimensional operations along with the read-out ultrasonic beam data, from the three-dimensional ultrasonic beam memory 8 also for input to the three-dimensional operation unit 21. The three-dimensional operation unit 21 is a look-up table (LUT) made of a RAM or ROM.

With the ultrasonic beam data accumulated in the ultrasonic beam data memory 5, a three-dimensional display order is issued. This causes the second embodiment, as with the first embodiment, to generate three-dimensional ultrasonic beam data q about one ultrasonic beam. The generating process is repeated to provide three-dimensional ultrasonic beam data Q with respect to a single visual angle. Three-dimensional ultrasonic beam data Q are generated for each of a plurality of different visual angles. The three-dimensional beam data Q thus acquired appear animated when displayed.

For a first round of the generation of three-dimensional ultrasonic beam data q, the address control unit 6 supplies the three-dimensional operation unit 21 with the address of LUT information independent of the three-dimensional ultrasonic beam data q from the three-dimensional ultrasonic beam data memory 8. The address control unit 6 supplies the ultrasonic beam data memory 5 with the address of ultrasonic beam data d subject to three-dimensional operations. The output of the three-dimensional operation unit 21 is held temporarily in a line memory 22 before being transferred to the three-dimensional ultrasonic beam data memory 8 when the bus becomes free. From a second and subsequent rounds of data generation, the address control unit 6 supplies the three-dimensional operation unit 21 with the address of LUT information corresponding to the three-dimensional ultrasonic beam data q from the three-dimensional ultrasonic beam data memory 8. The ultrasonic beam data memory 5 is furnished with the address of the ultrasonic beam data d subject to three-dimensional operations, and the three-dimensional ultrasonic beam data memory 8 is Xfed with the address of the three-dimensional ultrasonic beam data q. The output of the three-dimensional operation unit 21 is retained temporarily in the line memory 22 before being transferred to the three-dimensional ultrasonic beam data memory 8 when the bus becomes free. When all operations have ended, a three-dimensional display is effected.

As described, the ultrasonic diagnostic apparatus 200 practiced as the second embodiment of the invention generates three-dimensional ultrasonic beam data q by performing three-dimensional operations on ultrasonic beam data d. Because the amount of data to be processed is reduced, the ultrasonic diagnostic apparatus 200 in a simplified structure can display practical three-dimensional ultrasonic images in a short operation time. With the display suitably distorted to reflect the distance of the target object from the ultrasonic probe 1, the operator is allowed to become aware of that distance while watching the display. Furthermore, the inventive apparatus proceeds with its three-dimensional operations by simply transferring necessary data.

Third Embodiment

Figure 12:
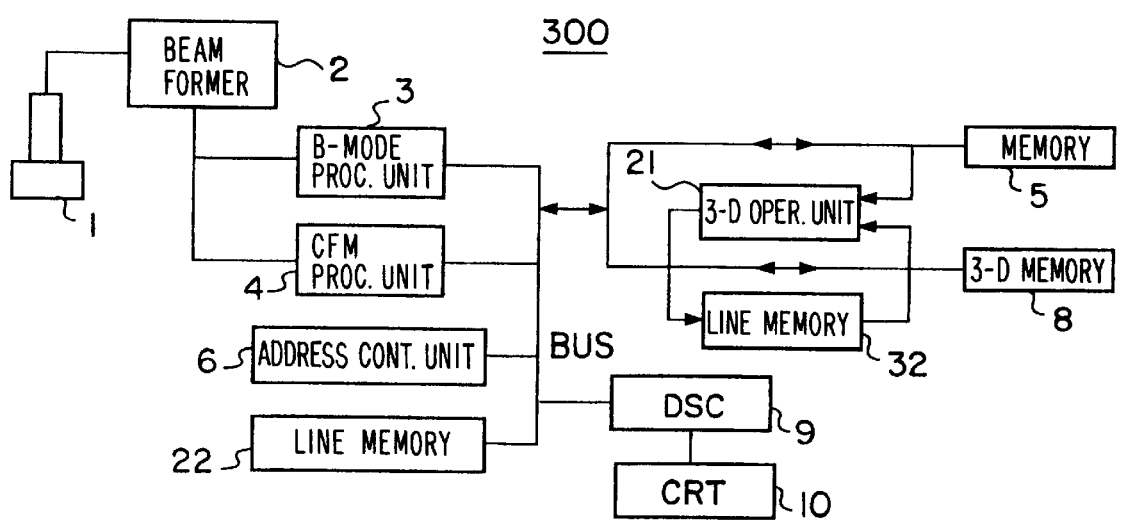
FIG. 12 is a block diagram of an ultrasonic diagnostic apparatus practiced as a third embodiment of the invention.

FIG. 12 is a block diagram of an ultrasonic diagnostic apparatus 300 practiced as the third embodiment of the invention. The ultrasonic diagnostic apparatus 300 has a local line memory 32 incorporated in the three-dimensional operation unit 21. By utilizing the local line memory 32, the three-dimensional operation unit 21 carries out three-dimensional operations at a higher speed than before.

Many widely different embodiments of the invention may be constructed without departing from the spirit and scope of the present invention. It should be understood that the present invention is not limited to the specific embodiments described in the specification, except as defined in the appended claims.

What is claimed is:

1. An ultrasonic diagnostic apparatus comprising:
   an ultrasonic probe for scanning planes of an object;
   data acquisition means for acquiring ultrasonic beam data by moving said ultrasonic probe in a direction substantially perpendicular to said planes;
   an ultrasonic beam data memory for storing ultrasonic beam data;
   a three-dimensional operation circuit for generating three-dimensional ultrasonic beam data by use of said ultrasonic beam data stored in said ultrasonic beam data memory so as to display a three-dimensional ultrasonic image of said object viewed from a desired line of sight;
   a digital scan converter for converting scans of said three-dimensional ultrasonic image to be displayed; and
   display means for displaying said three-dimensional ultrasonic image.

2. The apparatus of claim 1, further comprising an address control unit for sequentially writing and reading said ultrasonic beam data to and from said ultrasonic beam data memory in a direction of depth, and a three-dimensional ultrasonic beam data memory for storing said three-dimensional ultrasonic beam data.

3. The apparatus of claim 2, further comprising a line memory for temporarily holding output of said three-dimensional operation circuit.

4. An ultrasonic diagnostic apparatus of claim 3 wherein a physically identical memory is used as any one of said ultrasonic beam data memory, three-dimensional ultrasonic beam data memory and line memory.

5. An ultrasonic diagnostic apparatus of claim 3 wherein said address control unit reads said ultrasonic beam data and said three-dimensional ultrasonic beam data simultaneously from said ultrasonic beam data memory and from either said three-dimensional ultrasonic beam data memory or said line memory, and wherein said three-dimensional operation circuit generates said three-dimensional ultrasonic beam data based on said ultrasonic beam data and three-dimensional ultrasonic beam data read simultaneously.

6. An ultrasonic diagnostic apparatus of claim 5 further comprising:

a line memory for temporarily storing said three-dimensional ultrasonic beam data generated by said three-dimensional operation circuit; and
an address control unit for transferring said three-dimensional ultrasonic beam data from said line memory to said three-dimensional ultrasonic beam data memory at a next timing.

7. An ultrasonic diagnostic apparatus of claim 4, wherein said address control unit reads said ultrasonic beam data and said three-dimensional ultrasonic beam data simultaneously from said ultrasonic beam data memory and from either said three-dimensional ultrasonic beam data memory or said line memory, and wherein said three-dimensional operation circuit generates said three-dimensional ultrasonic beam data based on said ultrasonic beam data and three-dimensional ultrasonic beam data read simultaneously.

8. An ultrasonic diagnostic apparatus of any one of claims 1 through 6 and 7 further comprising a bus for data transfer in B mode and CFM (color flow mapping) mode, said bus being used to carry out at least part of said transfer of said ultrasonic beam data and three-dimensional ultrasonic beam data.

9. An ultrasonic diagnostic apparatus of any one of claims 5 through 6 and 7 wherein said three-dimensional operation circuit is a look-up table (LUT) made of either a RAM (random access memory) or a ROM (read only memory) storing LUT information corresponding to said three-dimensional ultrasonic beam data input either from said three-dimensional ultrasonic beam data memory or from said line memory, as well as LUT information independent of said three-dimensional ultrasonic beam data, and wherein said address control unit selects the type of LUT information to be used.

10. An ultrasonic diagnostic apparatus of any one of claims 3, 4, 5, 6 and 7 wherein said address control unit, in generating three-dimensional ultrasonic beam data based on said ultrasonic beam data, calculates an ultrasonic beam address of said three-dimensional ultrasonic beam data to be read either from said three-dimensional ultrasonic beam data memory or from said line memory by use of a formula:

$$N + F \cdot D \cdot \tan\{T\} + \text{Toffset}$$

where, F stands for a frame number of ultrasonic beam data, N for an ultrasonic beam address, D for a frame-to-frame distance, T for a horizontal visual angle, and Toffset for an amount of horizontal offset.

11. An ultrasonic diagnostic apparatus of any one of claims 3, 4, 5, 6 and 7 wherein said address control unit, in generating three-dimensional ultrasonic beam data based on said ultrasonic beam data, calculates a depth address of said three-dimensional ultrasonic beam data to be read either from said three-dimensional ultrasonic beam data memory or from said line memory by use of a formula:

$$M + F \cdot D \cdot \tan\{U\} + \text{Uoffset}$$

where, F stands for a frame number of ultrasonic beam data, M for a depth address, D for a frame-to-frame distance, U for a vertical visual angle, and Uoffset for an amount of vertical offset.

12. An ultrasonic diagnostic apparatus of any one of claims 1 through 6 and 7 wherein said ultrasonic beam data is either one or a combination of a flow rate obtained either in B mode or in color flow mapping mode, a flow rate acquired either from power or from second harmonic, and power.

* * * * *